US010624860B2

United States Patent
Boday et al.

(10) Patent No.: US 10,624,860 B2
(45) Date of Patent: Apr. 21, 2020

(54) METHOD TO GENERATE MICROCAPSULES WITH HEXAHYDROTRIAZINE (HT)-CONTAINING SHELLS

(71) Applicant: International Business Machines Corporation, Armonk, NY (US)

(72) Inventors: Dylan J. Boday, Tucson, AZ (US); Jeannette M. Garcia, San Leandro, CA (US); James L. Hedrick, Pleasanton, CA (US); Brandon M. Kobilka, Tucson, AZ (US); Jason T. Wertz, Pleasant Valley, NY (US); Rudy J. Wojtecki, San Jose, CA (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/465,252

(22) Filed: Mar. 21, 2017

(65) Prior Publication Data

US 2018/0271793 A1    Sep. 27, 2018

(51) Int. Cl.
*A61K 9/58* (2006.01)
*A61K 9/50* (2006.01)

(52) U.S. Cl.
CPC ............ *A61K 9/5031* (2013.01); *A61K 9/501* (2013.01); *A61K 9/5015* (2013.01); *A61K 9/5026* (2013.01)

(58) Field of Classification Search
CPC ..... A61K 9/501; A61K 9/5015; A61K 9/5026
USPC ....................................................... 514/241
See application file for complete search history.

(56) References Cited

U.S. PATENT DOCUMENTS

| | | | |
|---|---|---|---|
| 5,225,278 A * | 7/1993 | Kielbania, Jr. | ........ A01N 25/28 264/4.3 |
| 6,294,570 B1 | 9/2001 | Krause et al. | |
| 6,518,330 B2 | 2/2003 | White et al. | |
| 8,491,992 B2 | 7/2013 | Schmidt et al. | |
| 9,271,498 B2 | 3/2016 | Boday et al. | |
| 9,352,045 B2 | 5/2016 | Boday et al. | |
| 2004/0258753 A1 | 12/2004 | Demeester et al. | |
| 2010/0099793 A1 | 4/2010 | Wunder | |
| 2011/0039980 A1 | 2/2011 | Caruso et al. | |
| 2013/0122070 A1* | 5/2013 | Barnett | .................... A61K 8/11 424/401 |

OTHER PUBLICATIONS

Brown et al., In situ poly(urea-formaldehyde) microencapsulation of dicyclopentadiene, J. Microencapsulation, Nov.-Dec. 2003, vol. 20 No. 6, 719-730.

* cited by examiner

*Primary Examiner* — Craig D Ricci
*Assistant Examiner* — Janet L. Coppins
(74) *Attorney, Agent, or Firm* — Patterson + Sheridan, LLP

(57) ABSTRACT

Materials and methods for preparing a payload-containing microcapsule with walls that have hexahydrotriazine (HT) and/or hemiaminal (HA) structures are disclosed. To an HT small molecule or a HA small molecule, or a combination thereof, in a solvent is added a cross-linking agent, $NH_4Cl$, and a copolymer. The solution is acidified, and a payload agent is added. The HT small molecule and HA small molecule may have orthogonal functionality.

20 Claims, 1 Drawing Sheet

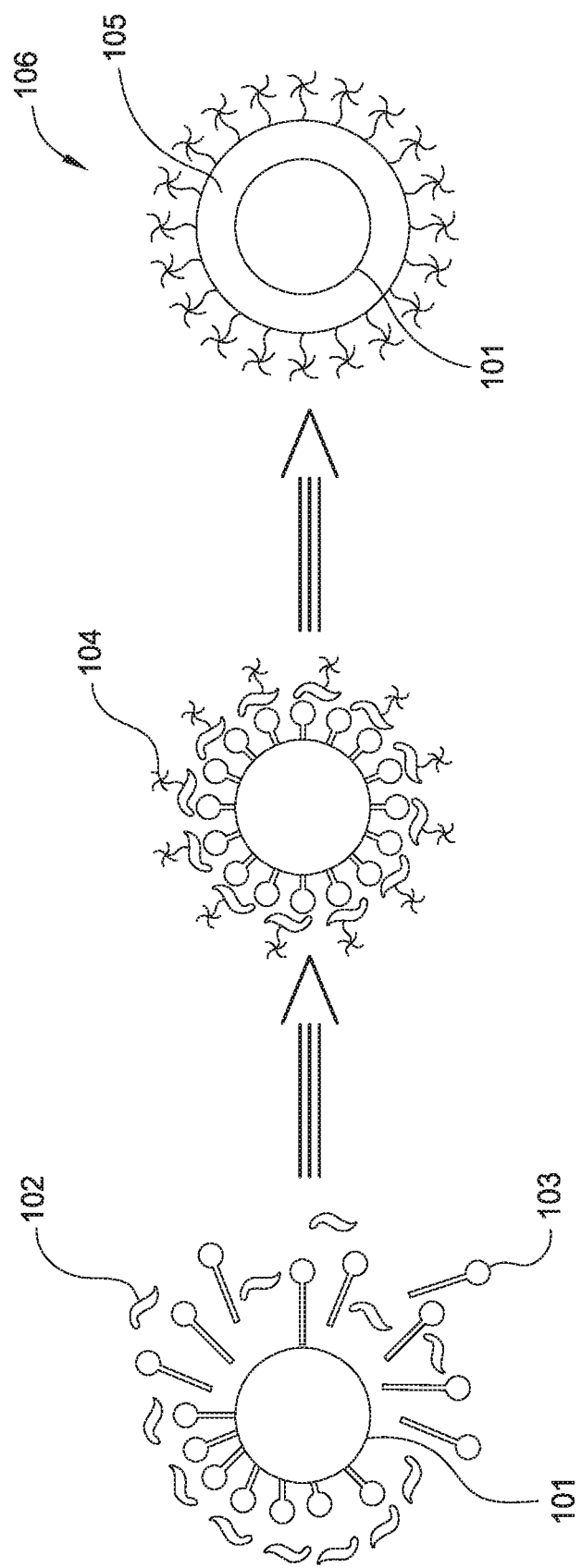

METHOD TO GENERATE MICROCAPSULES WITH HEXAHYDROTRIAZINE (HT)-CONTAINING SHELLS

FIELD OF THE DISCLOSURE

Materials and methods described herein relate to encapsulated payloads.

BACKGROUND

Microcapsules may be used as release systems for various types of materials (also referred to as "payloads"). Examples of payloads may include perfume oils, repellants, self-healing agents, or disinfecting agents, among other alternatives. Rupturing the microcapsule, and release of the payload, may depend on mechanically breaking a polymer shell of the microcapsule. For example, the polymer shell may be broken by scratching, puncturing, or other mechanical means directly applied to a polymeric surface of the microcapsule.

SUMMARY

Embodiments described herein relate to methods of making microcapsules that have hexahydrotriazine (HT), hemiaminal (HA) functionality, or a combination thereof.

According to one embodiment, a method of making microcapsules is provided. The method includes forming a mixture comprising a hexahydrotriazine material, a hemiaminal material or a combination thereof, a cross-linking agent, a copolymer, and a solvent; acidifying the solution; and adding a payload agent.

According to another embodiment, a method of making microcapsules is provided. The method includes forming a mixture comprising an orthogonal-functionalized hexahydrotriazine small molecule or an orthogonal-functionalized hemiaminal small molecule, or a combination thereof, a cross-linking agent, $NH_4Cl$, a copolymer, and a solvent, wherein at least one of the orthogonal-functionalized hexahydrotriazine material or orthogonal-functionalized hemiaminal material comprises the structure

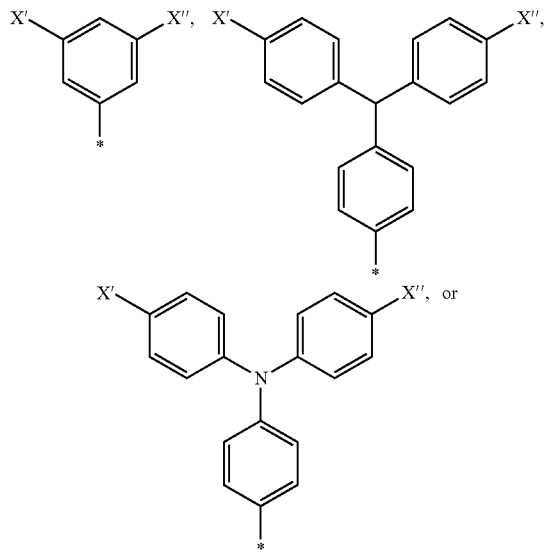

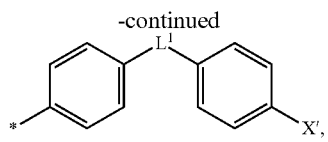

wherein X' and X" is selected from a group consisting of —OH, —O—, —NH$_2$, —NH—, —N(R$^1$)H, —N(R$^1$)—, —SH, —S—, —SO$_2$, —OR$^2$, and —R$^3$, and combinations thereof, wherein R$^1$, R$^2$, and R$^3$ independently comprise at least 1 carbon; acidifying the solution; and adding a payload agent.

According to another embodiment, a microcapsule is provided. The microcapsule comprises at least one hexahydrotriazine material or hemiaminal material, or a combination thereof; and at least one component covalently linked to the hexahydrotriazine material or hemiaminal material, wherein the component comprises the structure

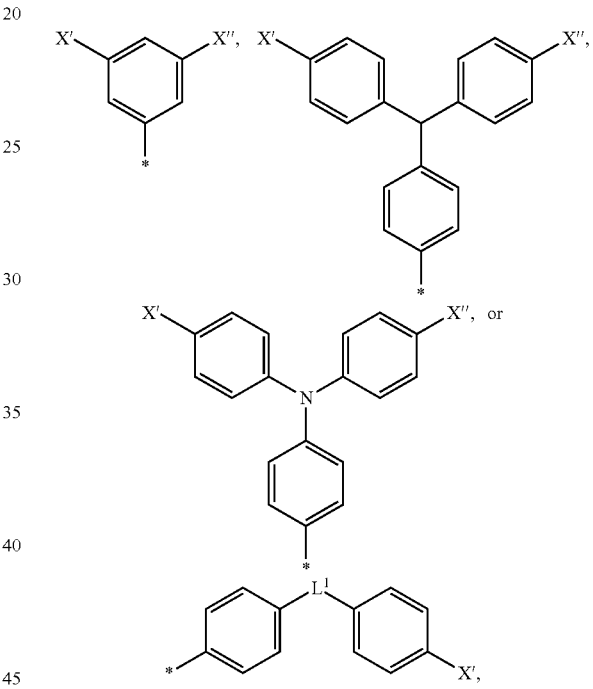

wherein X' and X" is selected from a group consisting of —OH, —O—, —NH$_2$, —NH—, —N(R$^1$)H, —N(R$^1$)—, —SH, —S—, —SO$_2$, —OR$^2$, and —R$^3$, and combinations thereof, wherein R$^1$, R$^2$, and R$^3$ independently comprise at least 1 carbon.

Features and other benefits that characterize embodiments are set forth in the claims annexed hereto and forming a further part hereof. However, for a better understanding of the embodiments, and of the advantages and objectives attained through their use, reference should be made to the Drawings and to the accompanying descriptive matter.

BRIEF DESCRIPTION OF THE SEVERAL VIEWS OF THE DRAWINGS

FIG. 1 is an example of the formation of a microcapsule having an encapsulated payload.

DETAILED DESCRIPTION

The present disclosure relates to the formation of microcapsules having an encapsulated payload. In the present disclosure, the payload is incorporated into a nanocapsule or microcapsule with a polymeric wall that has HT moieties, HA moieties, or a combination thereof. The HT and HA moieties may have additional orthogonal functionality, which would allow for covalent bonding of other moieties to the polymer matrix (also referred to as a "polymer shell"). After incorporation into a polymeric matrix, an end user can rupture the capsules by various means, including utilizing the chemical properties of the HT and HA moieties.

Microcapsules are widely used as release systems containing, for example, self-healing agents, disinfectants, and repellants. The rupture and eventual release of the payload is dependent on breaking the polymer shell, which is typically done mechanically through scratching, puncturing, or other mechanical means directly applied to the polymer surface. The microcapsules described herein may be opened mechanically or chemically, as described further below.

As used herein, the term "microcapsule" is used to refer to capsules that are in a range of about 10 microns to 1000 microns in diameter. However, it will be appreciated that the following disclosure may be applied to capsules having a smaller size (also referred to as "nanocapsules").

Advantageously, HT improves the physical and thermal properties of the materials. Polymers containing HT repeat units are quite strong, and can be depolymerized by subjecting the polymer to chemical environments that debond the HT structures in the polymer. The strength of the HT unit is believed to proceed from the triazine ring structure, which has three branching points. Including sufficient HT repeat units in the polymer can result in microcapsules effectively susceptible only to chemical opening and resistant to mechanical breakage. The unique properties of HT moieties allow for chemically triggered release of payloads under controlled conditions without unintended mechanical release.

Advantageously, the orthogonal-functionalized HT and orthogonal-functionalized HA allow for covalent bonding into a polymer matrix, such as a polymeric resin, thus, allowing for more sensitive detection of cracks in the matrix. Typically, in composite containing microcapsules, crack propagation is used to rupture and release the payload. By bonding the capsule to the matrix, there is a higher likelihood of rupture due to crack propagation that does not necessarily go through the capsule. In contrast, by bonding the capsule to the matrix, one can utilize the forces that pull the capsule apart as the matrix separates.

Advantageously, these microcapsules with walls that have HT and HA structures can be generated with homogenous size distributions, and can be made to avoid releasing payloads in undesirable situations, making the microcapsules environmentally friendly. HT and HA moieties can also be utilized as a functional filler for polymer composites that will increase mechanical strength of the composite. Additionally, the microcapsules can be incorporated at various volumes depending on the amount of payload agent(s) that might be needed, can be used as a flow controller replacement for nano-silica, and microcapsules' homogeneous size allows for a controlled release of payload agent per unit area.

Advantageously, these microcapsules can find usage in multiple applications including pharmaceutical products, insulation technologies, printed circuit boards, bezels, smart textiles, agricultural products, and consumer products such as food products, household products, and personal care products.

This disclosure includes chemical structures that show atomic compositions of compounds and relative bonding arrangements of atoms in a chemical compound. Unless specifically stated, the geometric arrangement of atoms shown in the chemical structures is not intended to be an exact depiction of the geometric arrangement of every embodiment, and those skilled in the chemical arts will recognize that compounds may be similar to, or the same as, the illustrated compounds while having different molecular shapes or conformations. For example, the structures denoted herein may show bonds extending in one direction, while embodiments of the same compound may have the same bond extending in a different direction. Additionally, bond lengths and angles, Van der Waals interactions, isoelectronic structures, and the like may vary among instances of the same chemical compound. Additionally, unless otherwise noted, the disclosed structures cover all stereoisomers, conformers, rotamers, isomers, enantiomers, of the represented compounds.

Numbered chemical structures are numbered using numbers, or numbers and letters, in parentheses. Numbered chemical reaction schemes are numbered using numbers, or numbers and letters, in square brackets. Unless otherwise noted, chemical reactions are performed at ambient conditions or under slight heating with no special atmosphere or head space, and may be performed using standard organic solvents to manage mix properties such as viscosity and flow index.

FIG. 1 shows formation of an exemplary payload-filled microcapsule. The shells of the microcapsule may comprise HT and HA moieties, or a combination thereof, and the moieties may be orthogonally functionalized. In FIG. 1, payload-filled microcapsules comprising orthogonal functionality 106 are formed using an oil-in-water emulsion technique to create a protective polymeric shell 105 around a payload core.

In the example of FIG. 1, a payload 101 represents an oil phase that is dispersed into an aqueous continuous phase and stirred to begin an emulsion process. As illustrative, non-limiting examples, the payload 101 (or multiple payloads) may include a perfume oil, a self-healing agent, a disinfectant, a repellant, or a combination thereof. One example of a payload agent 101 that may be used is a latent curing agent such as N-ethylpiperazine. It will be appreciated that various payload(s) may be selected to provide various functionalities for various applications. Other possible payloads 101 could be polymerizable molecules such as cyclic olefins, norbornene, substituted norbornene, cyclooctadiene, substituted cyclooctadiene, lactones, acrylates, acrylic acids, styrenes, isoprene, butadiene, isocyanate functional groups with hydroxyl functional groups, and epoxies. In some cases, these agents may require an activator such as a catalyst and/or initiator. Additionally, solvents could be incorporated into the capsules which could be chosen from aprotic solvents, protic solvents, or a mixture of the two.

A cross-linking agent 102, such as formaldehyde, is reacted with a polymeric emulsifying agent 103, such as ethylene maleic anhydride copolymer, urea (or melamine), and an orthogonal-functionalized HT small molecule 104 to generate a capsule wall around the payload. Other cross-linking agents 102 may be used including glutaraldehyde, di-acid chloride, and derivatives thereof. Other polymeric emulsifying agents 103 may be used including whey protein isolate, sodium caseinate, a surfactant, and derivatives thereof. Particle size may be controlled by adjusting a stir speed during the reaction. For example, a faster stir speed may result in formation (on average) of smaller ("finer") particles than a slower stir speed.

The second part of the reaction diagram of FIG. 1, illustrates that a curing stage may be used to complete the reaction between the cross-linking agent and the polymeric emulsifying agent to form the microcapsules or nanocapsules, depending on a stir speed. These nanocapsules or microcapsules are then incorporated within a polymeric matrix 105 (also referred to as a polymeric shell) to which they would covalently bind. The amount of nanocapsules or microcapsules needed is empirically determined based on the rheology of the resins, the particle size of the nanocapsule or microcapsule, and the amount needed to reach the desired payload content for release.

In another embodiment, the orthogonal-functionalized HT small molecule 104 may also be an orthogonal-functionalized hemiaminal, a hexahydrotriazine small molecule, a hemiaminal small molecule, or a combination thereof. The orthogonal-functionalized HT and HA small molecules may be mono-, di-, or tri-functionalized. The general procedure for making the microcapsule, as shown below, may be used.

Example Preparation of Microcapsule Having HT-112 and/or HA-112

The payload-containing microcapsule with walls that have HT structures, HA structures, or a combination thereof, may be prepared according to the following exemplary process. To a stirring aqueous solution containing an ethylene maleic anhydride (EMA) copolymer surfactant, urea (or melamine), and ammonium chloride ($NH_4Cl$), an orthogonal-functionalized HT small molecule (for example, HT-112), or an orthogonal-functionalized HA small molecule (for example, HA-112), or a combination thereof, may be added. The pH may be adjusted to about 3.5 by adding NaOH and HCl (or other suitable acids and bases), followed by the addition of an emulsifying agent (for example, a self-healing agent). The payload may be added with other ingredients, such as monomers and/or pre-polymers, stabilizers, solvents, viscosity modifiers, odorants, colorant/dyes, blowing agents, antioxidants, or co-catalysts, or a combination thereof. Formaldehyde (or other suitable cross-linking agents) is added, which acts as a curing agent to complete the polymeric shell formation. The resulting microcapsules may be subsequently washed and sieved to remove unreacted material.

In another embodiment, the HT small molecule (for example, HT-111), HA small molecule (for example, HA-111), or a combination thereof may be used in making the microcapsules. The microcapsule containing, for example, HT-111 and/or HA-111 may be made by the same process as described above.

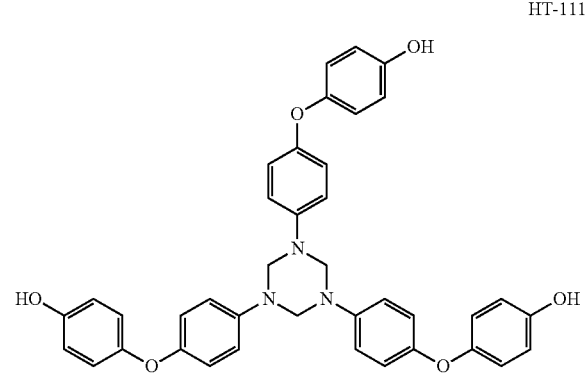

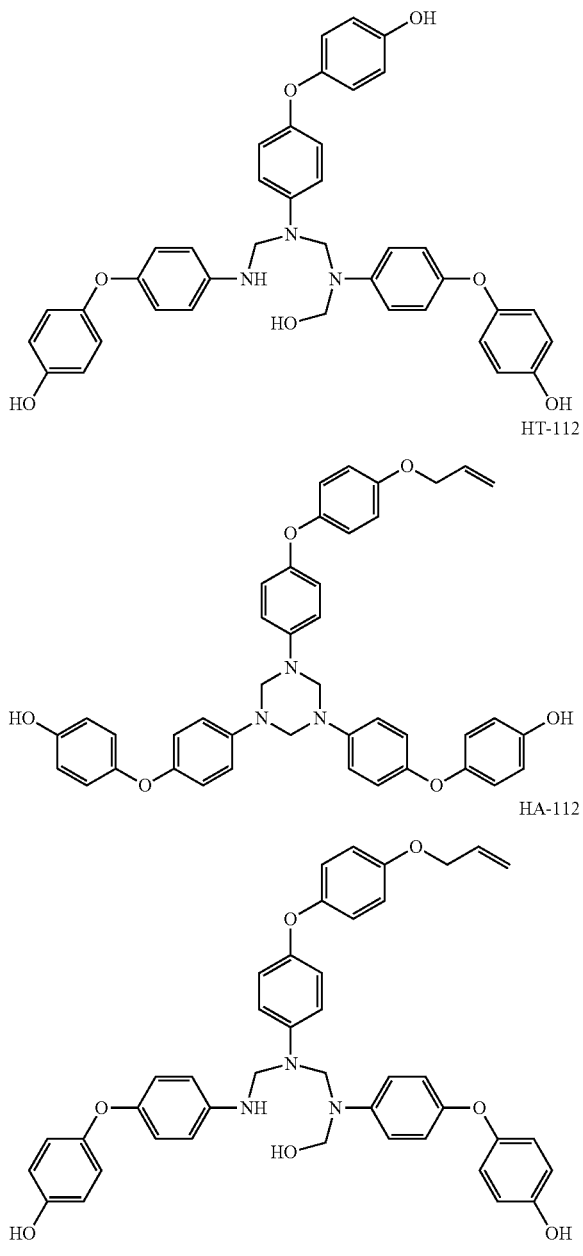

Thus, FIG. 1 illustrates a particular embodiment of a process of producing a microcapsule (having an encapsulated payload). The capsule may be generated from HT small molecules, HA small molecules, orthogonal-functionalized HT small molecules, orthogonal-functionalized HA small molecules, or a combination thereof. The payload is incorporated into a polymeric nanocapsule or microcapsule that is generated containing HT moieties, HA moieties, or a combination thereof. The HT- and HA-containing blocks may have orthogonal functionality, affording the ability to covalently bind to the polymeric matrix. After incorporation of these new microcapsules into a polymeric matrix, an end user can rupture the capsules by various means, including using the recyclability of the HT and HA moieties. An end user may also rupture and release the payload via scratching, puncturing, or other mechanical means, or recycling of the HT and HA small molecules.

All varieties of the HA and HT small molecules described herein will participate in the emulsion polymerization to form the microcapsule.

Example Preparation of Microcapsule Having HT-113 and/or HA-113

Example Preparation of Microcapsule Having HT-114 and/or HA-114

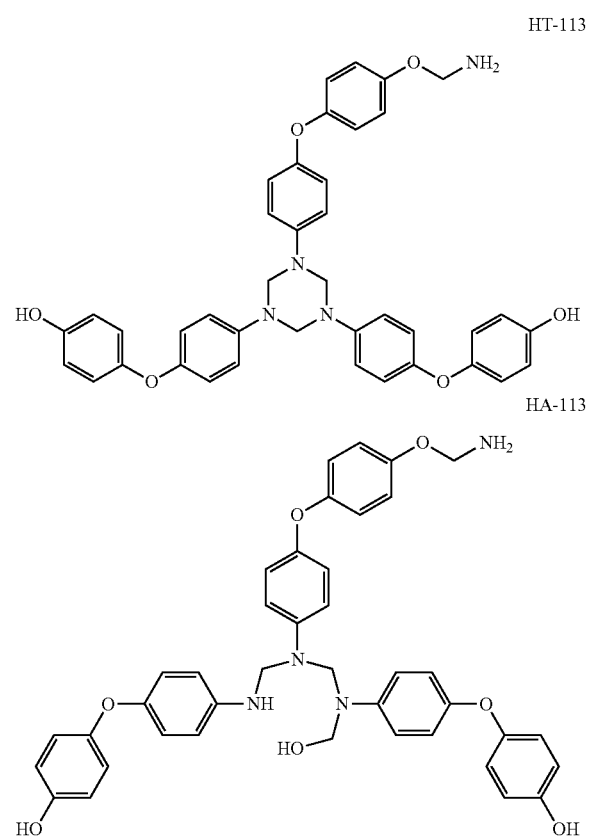

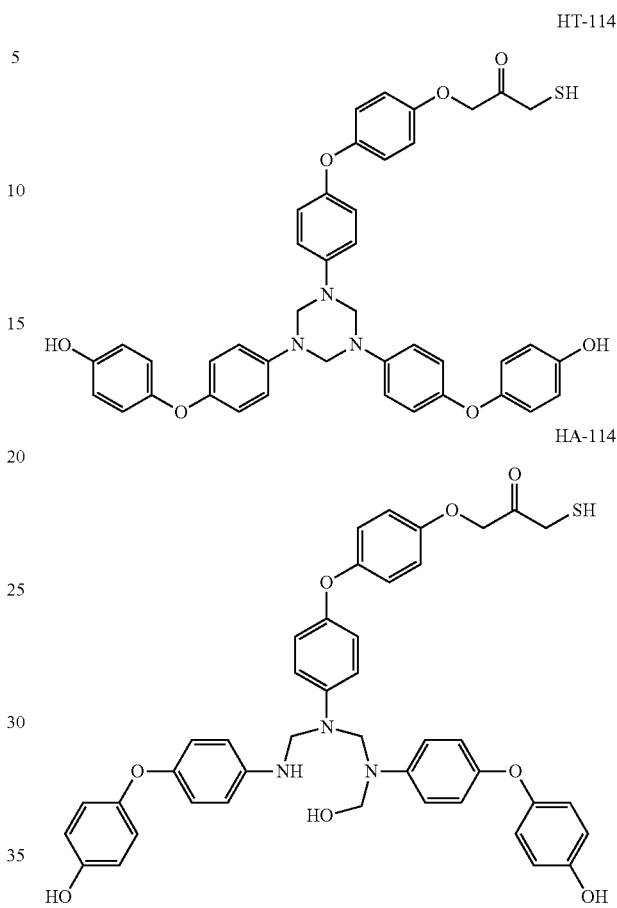

To a stirring aqueous solution containing an ethylene maleic anhydride (EMA) copolymer surfactant, urea (or melamine), and ammonium chloride (NH$_4$Cl), an orthogonal-functionalized HT small molecule (for example, HT-113), an orthogonal-functionalized HA small molecule (for example, HA-113), or a combination thereof, may be added. The pH may be adjusted to about 3.5 by adding NaOH and HCl (or other suitable acids and bases), followed by the addition of an emulsifying agent (for example, a self-healing agent). The payload may be added with other ingredients, such as monomers and/or pre-polymers, stabilizers, solvents, viscosity modifiers, odorants, colorant/dyes, blowing agents, antioxidants, or co-catalysts, or a combination thereof. Formaldehyde is added, which acts as a curing agent to complete the polymeric shell formation. The resulting microcapsules may be subsequently washed and sieved to remove unreacted material.

To a stirring aqueous solution containing an ethylene maleic anhydride (EMA) copolymer surfactant, urea (or melamine), and ammonium chloride (NH$_4$Cl), an orthogonal-functionalized HT small molecule (for example, HT-114), an orthogonal-functionalized HA small molecule (for example, HA-114), or a combination thereof, may be added. The pH may be adjusted to about 3.5 by adding NaOH and HCl (or other suitable acids and bases), followed by the addition of an emulsifying agent (for example, a self-healing agent). The payload may be added with other ingredients, such as monomers and/or pre-polymers, stabilizers, solvents, viscosity modifiers, odorants, colorant/dyes, blowing agents, antioxidants, or co-catalysts, or a combination thereof. Formaldehyde is added, which acts as a curing agent to complete the polymeric shell formation. The resulting microcapsules may be subsequently washed and sieved to remove unreacted material.

Scheme 1: Example Preparation of HT Small Molecules

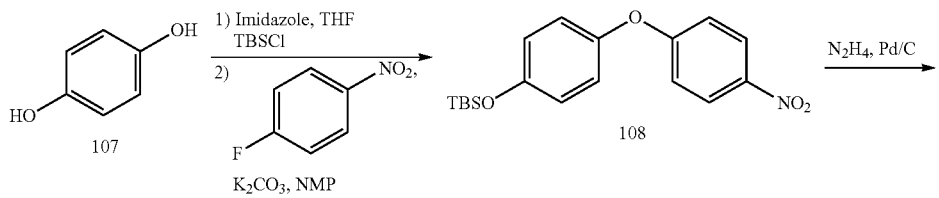

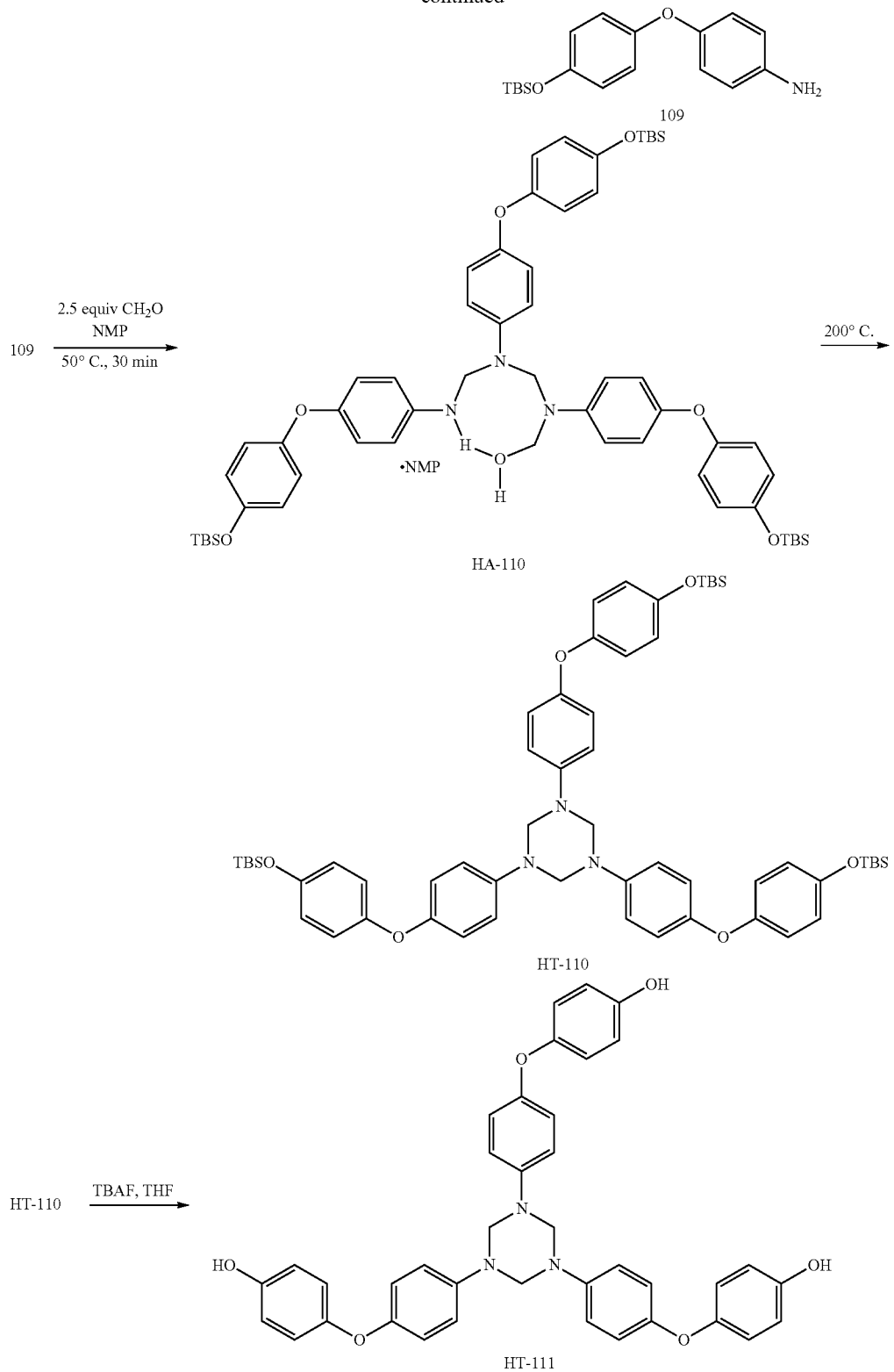

As an example of an embodiment, Scheme 1 shows formation of a hexahydrotriazine small molecule HT-111 from hydroquinone 107. To a solution of hydroquinone 107 in tetrahydrofuran (THF), at a temperature of about room temperature, is added imidazole and tert-butyldimethylsilyl chloride (TBSCl) to provide a monoprotected hydroquinone, not shown. The protecting group may be other groups such as a tetrydropyran group, an acetate group, or a methoxymethyl ether group. Those of ordinary skill in the art will recognize that other protecting groups and reaction conditions may be used. To a stirring solution of the monoprotected hydroquinone is added potassium carbonate ($K_2CO_3$) and 1-fluoro-4-nitrobenzene in a suitable solvent to give tert-butyldimethyl(4-(4-nitrophenoxy)phenoxy)silane 108. This addition may occur in any suitable solvent, including N-methyl-2-pyrrolidone (NMP) and dimethylformamide (DMF), at a temperature of about 80° C. to about 100° C. The nitro group of 108 is reduced to the corresponding aniline 109, 4-(4-((tert-butyldimethylsilyl)oxy)phenoxy) aniline, with hydrazine ($N_2H_4$) and palladium on carbon (Pd/C). For the reduction, the Pd/C catalyst, in the form of a powder, is stirred into the mixture with $N_2H_4$. Alternately, the Pd/C catalyst and $N_2H_4$ can be dispersed or dissolved in any suitable solvent to form a solution, which is then added to the reaction mixture. The reduction may occur in any suitable solvent, including ethanol and NMP, at a temperature of about room temperature or elevated temperature, up to about 100° C.

1,3,5-tris(4-(4-((tert-butyldimethylsilyl)oxy)phenoxy) phenyl)-1,3,5-triazinane (HT-110) is then formed by reaction of aniline 109 with a formaldehyde material (i.e., formaldehyde or paraformaldehyde) in the presence of N-methyl-2-pyrrolidinone. Aniline 109 and formaldehyde are dissolved in a solvent such as N-methyl-2-pyrrolidone, and mixed. The reaction mixture is heated gently while mixing. Usable solvents for the reaction include any suitable solvents, including dipolar aprotic solvents such as, for example, N-methyl-2-pyrrolidone (NMP), dimethyl sulfoxide (DMSO), N,N-dimethylformamide (DMF), N,N-dimethylacetamide (DMA), propylene carbonate (PC), and propylene glycol methyl ether acetate (PGMEA). Most preferably, the solvent is NMP. The reaction may be performed at temperatures of about 50° C. to about 200° C.

Performing the reaction at lower temperatures, for example below about 80° C., forms a hemiaminal, for example, ((4-(4-((tert-butyldimethylsilyl)oxy)phenoxy)phenyl)(((4-(4-((tert-butyldimethylsilyl)oxy)phenoxy)phenyl) (((4-(4-((tert-butyldimethylsilyl)oxy)phenoxy)phenyl) amino)methyl)amino)methyl)amino)methanol (HA-110). HA-110 is shown in its hydrogen bonded form, coordinated with NMP. The reaction proceeds through the hemiaminal stage at low temperatures, and at higher temperatures water is eliminated as the free amine and hydroxyl groups react to close the ring. Thus, an HA, HT, or a mixture of HA and HT may be formed depending on how the reaction is performed. If the reaction is performed for an extended time at a temperature above about 80° C., the material will be an HT. If the reaction temperature never exceeds 80° C., the material will be mostly, or entirely, HA. If the reaction is performed for a time at a temperature between about 50° C. and about 80° C., and then continued at a temperature above about 80° C. for a limited time, a mixture of HA and HT units may be formed.

Triazine HT-110 and tetra-N-butylammonium fluoride (TBAF) are dissolved in THF, or any other suitable solvent, to perform the deprotection and provide HT small molecule 4,4',4"-(((1,3,5-triazinane-1,3,5-triyl)tris(benzene-4,1-diyl)) tris(oxy))triphenol (HT-111). This reaction may occur at temperatures of about 0° C. to about room temperature. This HT small molecule HT-111 may be used for the microcapsules. As mentioned above, those of ordinary skill in the art will recognize other protecting groups that may be used at earlier stages of the synthesis and subsequent reaction conditions that may be used to remove such protecting groups.

As shown in Scheme 2, and according to another embodiment, HA-110 can undergo deprotection. HA-110 and tetra-N-butylammonium fluoride (TBAF) are dissolved in THF, or any other suitable solvent, to perform the deprotection and provide HA small molecule 4-(4-((hydroxymethyl)(((4-(4-hydroxyphenoxy)phenyl)(((4-(4-hydroxyphenoxy)phenyl)amino)methyl)amino)methyl)amino)phenoxy)phenol (HA-111). This reaction may occur at temperatures of about 0° C. to about room temperature. In Scheme 2, HA-110 is shown in its non-hydrogen bonded form. Similarly, HA-111 is shown in its non-hydrogen bonded form.

Scheme 2: Example Preparation of HA Small Molecules

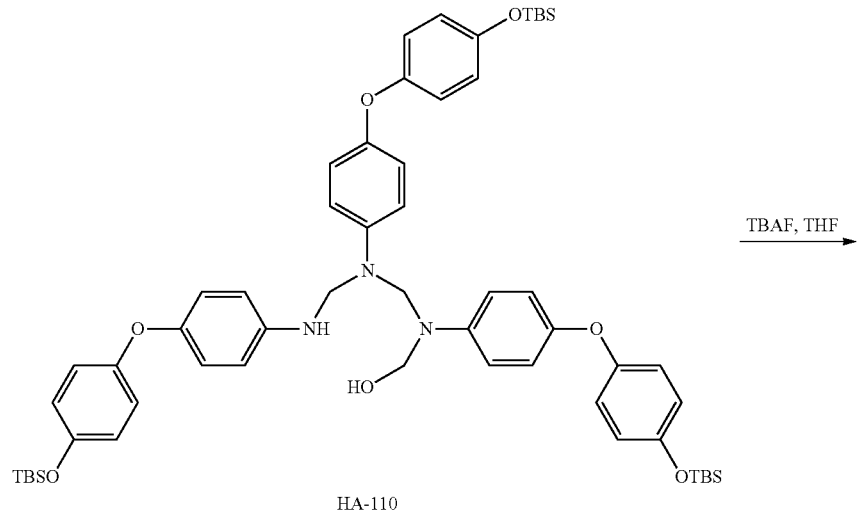

HA-110

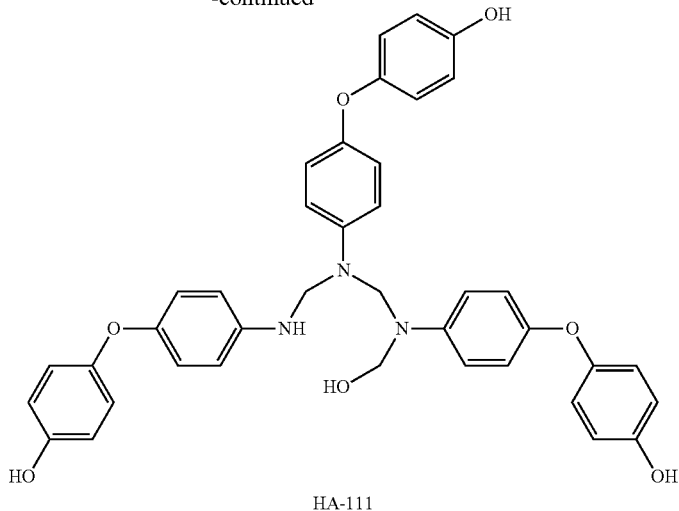

HA-111

As explained above, a mixture of both HA-110 and HT-110 may be formed. In such cases, the mixture may also be deprotected according to the procedures described herein.

It should be understood that other small molecules incorporating the hexahydrotriazine (HT) or hemiaminal (HA) core can be synthesized for use in the embodiments described herein. In one example, an HT and an HA can be represented by the structures

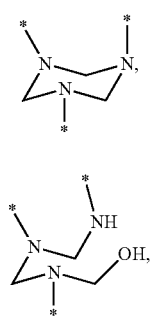

wherein the structure of formula (1) is an HT structure and the structure of formula (2) is a HA structure. Groups K' that may be part of the HT or HA small molecule may include the following structures:

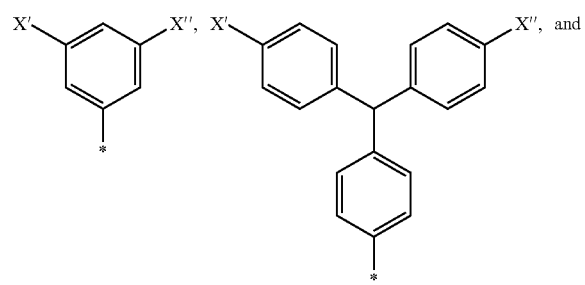

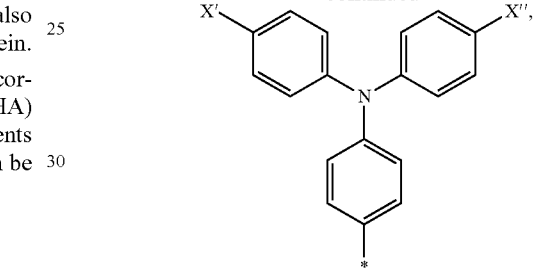

wherein X' and X" are each independently selected from the group consisting of —OH, —O—, —NH$_2$, —NH—, —N(R$^1$)H, —N(R$^1$)—, —SH, —S—, —SO$_2$, —OR$^2$, and —R$^3$, and combinations thereof, wherein R$^1$, R$^2$, and R$^3$ independently comprise at least 1 carbon. X' and X" may be an alkoxy group, including oligo(ethylene glycol), poly(ethylene glycol), or an alkene group, including vinyl and allyl.

Structures containing X' and X" (such as, where X' and X" are —OH, —O—, —NH$_2$, —NH—, —N(R$^1$)H, —N(R$^1$)—, —SH, —S—, and —SO$_2$) would have protecting groups during the synthesis of HA and HT small molecules. Suitable protecting groups include tosyls for amines, ethynyl p-tolyl sulphones (tosylacetylene) for thiols, and tert-butyldimethylsilyl ethers for alcohols. Those of ordinary skill in the art will recognize other suitable protecting groups, reaction conditions, and deprotecting agents that can be used during the synthesis of HA and HT small molecules incorporating such groups.

Other groups K' usable for the HT and HA small molecules described herein may have at least one 6-carbon aromatic ring. A category of such groups may be represented by the structure of formula (3)

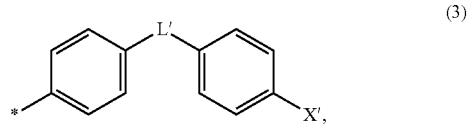

wherein L' is selected from the group consisting of —O—, —S—, —N(R⁴)—, —N(H)—, —R⁵—, and combinations thereof, wherein R⁴ and R⁵ independently comprise at least 1 carbon; and wherein X' is selected from the group consisting of —OH, —O—, —NH₂, —NH—, —N(R¹)H, —N(R¹)—, —SH, —S—, —SO₂, —OR², and —R³, and combinations thereof, wherein R¹, R², and R³ independently comprise at least 1 carbon. X' may be an alkoxy group, including oligo(ethylene glycol), poly(ethylene glycol), or an alkene group, including vinyl and allyl.

In an embodiment, R⁴ and R⁵ are independently selected from the group consisting of methyl, ethyl, propyl, isopropyl, phenyl, and combinations thereof. Other L' groups include methylene (—CH₂—), isopropylidenyl (—C(Me)₂-), and fluorenylidenyl

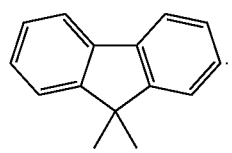

Structures containing X' and X" (such as, where X' and X" are —OH, —O—, —NH₂, —NH—, —N(R¹)H, —N(R¹)—, —SH, —S—, and —SO₂) would have protecting groups during the synthesis of HA and HT small molecules. Suitable protecting groups include tosyls for amines, ethynyl p-tolyl sulphones (tosylacetylene) for thiols, and tert-butyldimethylsilyl ethers for alcohols. Those of ordinary skill in the art will recognize other suitable protecting groups, reaction conditions, and deprotecting agents that can be used during the synthesis of HA and HT small molecules incorporating such groups.

Scheme 3: Example Preparation of Orthogonal-Functionalized HT Small Molecules

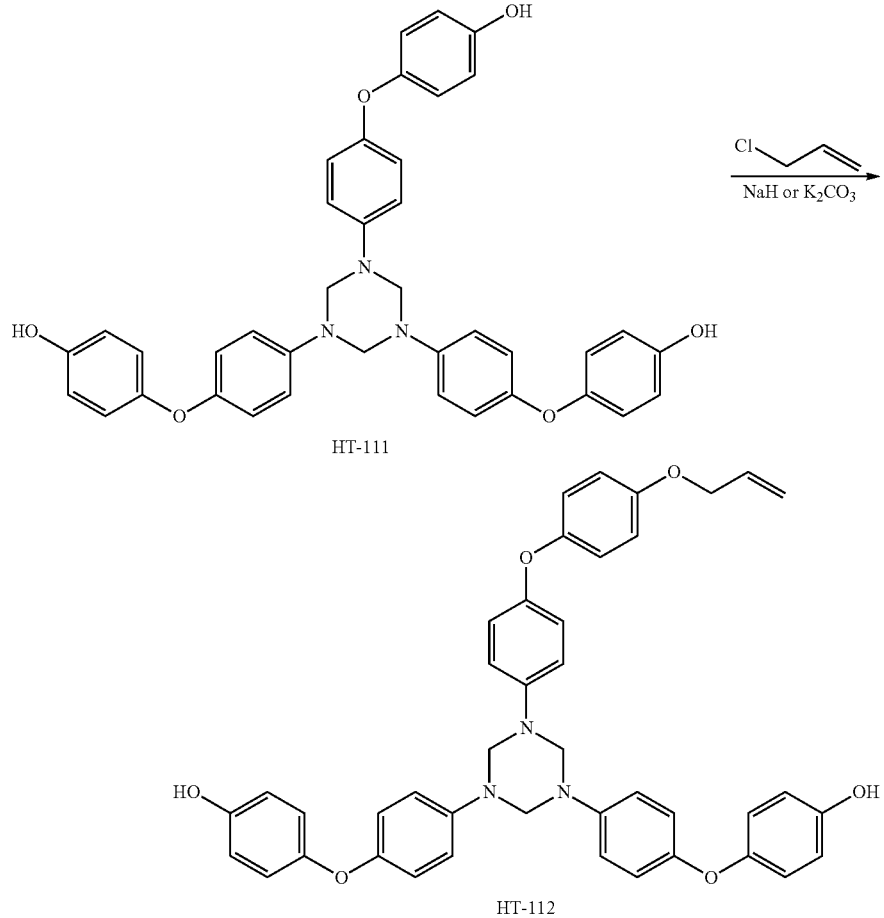

As an example of another embodiment and as shown in Scheme 3, an orthogonal-functionalized HT small molecule HT-112 may be prepared according to the following exemplary process. To a stirring solution of HT small molecule HT-111 in THF and/or ether, at a temperature of about 0° C. to about room temperature, is added a sodium hydride (NaH) suspension or potassium carbonate (K₂CO₃). Next, allyl chloride is added to the stirring solution which is maintained at a temperature of about 0° C. to about room temperature, and then allowed to warm to room temperature to give 4,4'-(((5-(4-(4-(allyloxy)phenoxy)phenyl)-1,3,5-triazinane-1,3-diyl)bis(4,1-phenylene))bis(oxy))diphenol (HT-112). For this reaction, any suitable base may be used, including a hydride base or a hydroxide base. Any suitable solvent for the reaction may be used, including ether and THF. A mixture of mono-, di-, and tri-functionalized allyl ethers may form from the reaction. The amount of mono-, di- and tri-functionalized allyl ethers can be controlled by stoichiometry and dilute conditions.

Microcapsules with orthogonal functionality at the surface thereof allow for the ability to bind (through, for example, the allyl group) into the polymer to increase rupture of the capsule, as described thereof. Moreover, microcapsules with orthogonal functionality can provide for dual functionality. For example, microcapsules with orthogonal functionality can be used for filler materials having orthogonal flame retardants on the outside of the capsule and a self-healing agent on the inside of the capsule.

Other examples of orthogonal groups (Y) include alkene-functionalized (via allyl chloride, for example), (meth)acrylate-functionalized (via (meth)acryloyl chloride, for example), and epoxy-functionalized resveratrol (via epichlorohydrin, for example) which can be used to react with the appropriate moiety within the polymeric resin. Other orthogonal groups (Y) include alkyne-functionalized (via propargyl chloride) that may be used for Click chemistry; and sulfur-functionalized (via mercaptoacetyl chloride Scheme 4: Example Preparation of Orthogonal-Functionalized HA Small Molecules

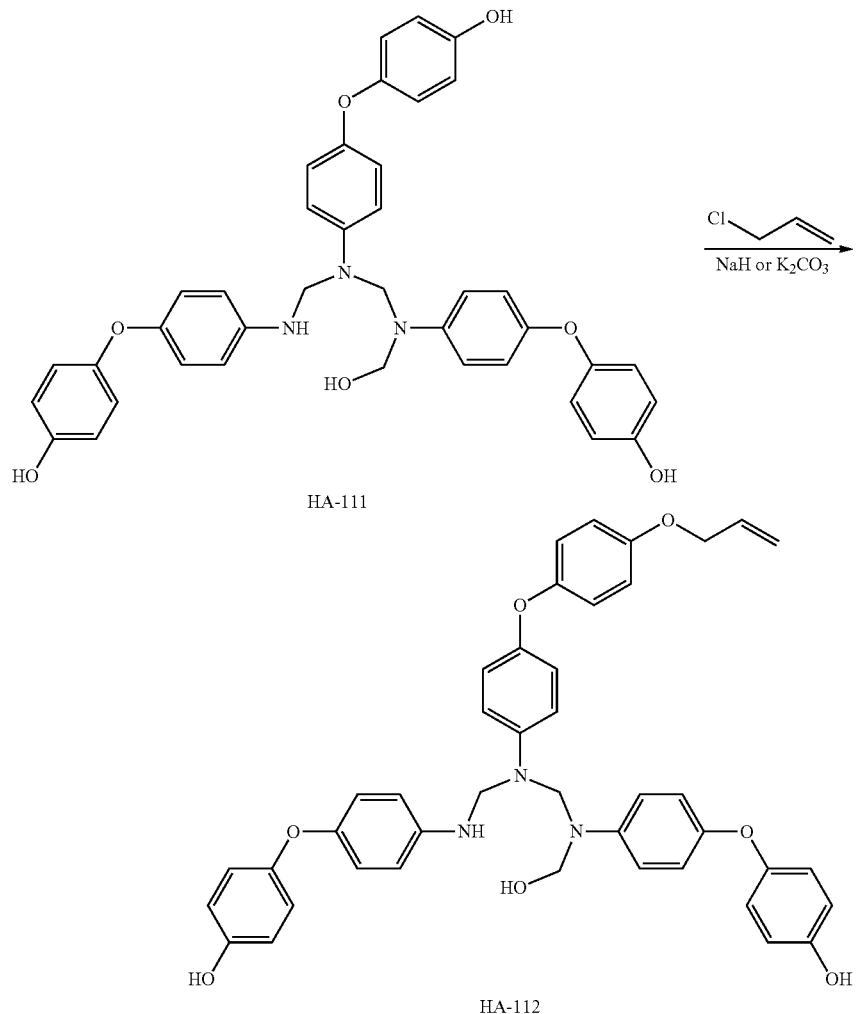

As an example of another embodiment and as shown in Scheme 4, HA-111 may be used as a precursor to prepare orthogonal-functionalized HA small molecules such as 4-(4-((((4-(4-(allyloxy)phenoxy)phenyl)(((4-(4-hydroxyphenoxy)phenyl)amino)methyl)amino)methyl)(hydroxymethyl)amino)phenoxy)phen ol (HA-112). HA-112 may be prepared according to the procedure described above. A mixture of mono-, di-, and tri-functionalized allyl ethers may form from the reaction. The amount of mono-, di- and tri-functionalized allyl ethers can be controlled by stoichiometry and dilute conditions.

The allyl-functionalized HT small molecule HT-112 and HA small molecule HA-112 are non-limiting examples of orthogonal-functionalized HT- and HA-small molecules.

or thiolalkylchloride) that may be used for thiol-ene or vulcanization chemistry. The thiol alkyl chloride can be protected, for example as a thioacetate, for the alkylation step. Other examples of orthogonal groups (Y) include the following structures

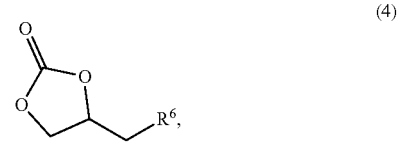

(4)

-continued

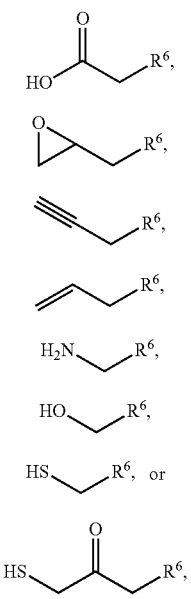

wherein R[6] is X' or X" of the HT or HA small molecule. During formation of the HT and HA, steps such as the formation of the hexahydrotriazine should be done at the lower end of the temperature range for compounds containing, for example, dioxolanone (4) or epoxide (6). Alternately, compounds containing epoxide (6) can be formed from hexahydrotriazine compounds containing allyl group (8) by reactions known by those skilled in the art. For example, after formation of the HT compound containing an allyl group, the solvent is removed by standard techniques known to those skilled in the art. Next, addition of meta-chloroperoxybenzoic acid (m-CPBA) to the HT compound containing an allyl group in dichloromethane, provides an HT compound containing an epoxide. Standard techniques of solvent removal should then be accomplished.

Additionally, the dioxolanone (4) may be formed after formation of the hexahydrotriazine by reaction of compounds hexahydrotriazine compounds containing epoxide group (6) known to those skilled in the art. For example, after formation of the HT compound containing the epoxide is formed (as described above), the epoxide can be converted to dioxolanone by using NMP as solvent, catalytic ethylene glycol and carbon dioxide (2 MPa), according to the general procedure of Liu, et al., BioResources, 8(3), 4218-4226, 2013. Prior to the conversion to dioxolanone, standard techniques of solvent removal should be accomplished. For other groups such as alcohols (10) amines (9), and thiols (11) and (12), the moieties should bear protecting groups prior to hexahydrotriazine formation as described above.

The orthogonal-functionalized HT small molecules may be mono-, di-, and tri-functionalized. The amount of mono-, di- and tri-functionalized orthogonal-functionalized HT small molecules can be controlled by stoichiometry and dilute conditions.

All varieties of the HT- and HA small molecules will participate in the emulsion polymerization to form the microcapsule described above.

The descriptions of the various embodiments of the present disclosure have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

While the foregoing is directed to embodiments of the present disclosure, other and further embodiments of the disclosure may be devised without departing from the basic scope thereof, and the scope thereof is determined by the claims that follow.

What is claimed is:

1. A method of making a microcapsule, comprising:
    forming a mixture comprising a hexahydrotriazine-based compound, a cross-linking agent, a copolymer, and a solvent, the hexahydrotriazine-based compound comprising a hexahydrotriazine having the structure

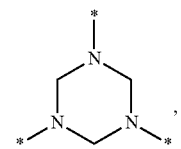

wherein at least one starred bond of the hexahydrotriazine represents a connection to a moiety of the hexahydrotriazine-based compound, the moiety having the structure

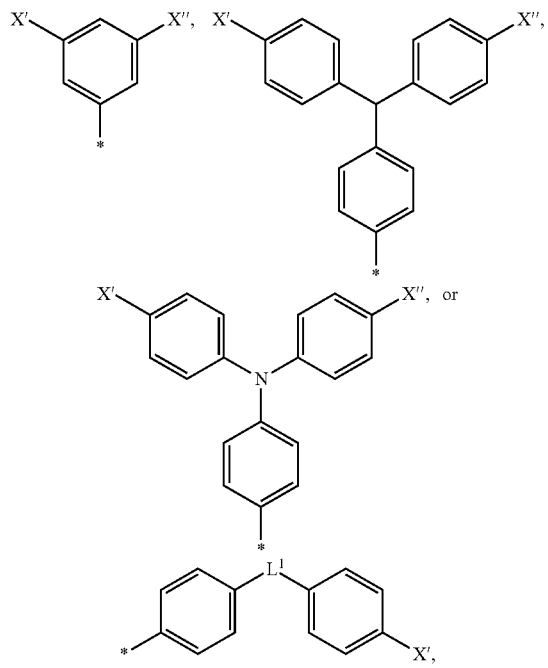

wherein:
    each of X' and X" is independently selected from the group consisting of —OH, —O—, —NH$_2$, —NH—, —N(R$^1$)H, —N(R$^1$)—, —SH, —S—, —SO$_2$, —OR$^2$, and —R$^3$, and combinations thereof,
    L' is selected from the group consisting of —O—, —S—, —N(R$^4$)—, —N(H)—, —R$^5$—, and combinations thereof, and each of $R^1$, $R^2$, $R^3$, $R^4$, and $R^5$ independently comprises at least 1 carbon;
adjusting a pH of the mixture by adding an acid or base; and
adding a payload agent.

2. The method of claim 1, wherein the mixture further comprises $NH_4Cl$.

3. The method of claim 1, wherein the mixture further comprises urea or melamine.

4. The method of claim 1, wherein the cross-linking agent is selected from the group consisting of formaldehyde, glutaraldehyde, di-acid chloride, and derivatives thereof.

5. The method of claim 1, wherein the copolymer is selected from the group consisting of ethylene maleic anhydride, whey protein isolate, sodium caseinate, a surfactant, and derivatives thereof.

6. The method of claim 1, further comprising curing the microcapsule by addition of formaldehyde, glutaraldehyde, di-acid chloride, or derivatives thereof.

7. The method of claim 1, wherein at least a portion of the hexahydrotriazine-based compound is a reaction product of a formaldehyde and an amine.

8. The method of claim 7, wherein the payload agent is a perfume oil.

9. The method of claim 7, wherein the payload agent is selected from the group consisting of cyclic olefins, norbornene, substituted norbornene, cyclooctadiene, substituted cyclooctadiene, lactones, acrylates, acrylic acids, styrenes, isoprene, butadiene, isocyanate functional groups with hydroxyl functional groups, and epoxies.

10. A method of making a microcapsule, comprising:
forming a mixture comprising a hexahydrotriazine-based compound, a cross-linking agent, a copolymer, and a solvent, the hexahydrotriazine-based compound comprising a hexahydrotriazine having the structure

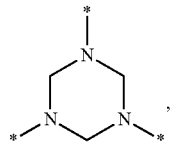

wherein at least one starred bond of the hexahydrotriazine represents a connection to a moiety of the hexahydrotriazine-based compound, the moiety having the structure

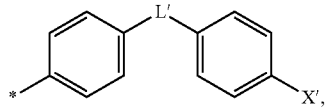

wherein:
X' is selected from the group consisting of —OH, —O—, —$NH_2$, —NH —, —N($R^1$)H, —N($R^1$)—, —SH, —S—, —$SO_2$, —$OR^2$, and —$R^3$, and combinations thereof,
L' is selected from the group consisting of —O—, —S—, —N($R^4$)—, —N(H)—, —$R^5$—, and combinations thereof, and
each of $R^1$, $R^2$, and $R^3$, $R^4$, and $R^5$ independently comprises at least 1 carbon,
adjusting a pH of the mixture; and
adding a payload agent.

11. The method of claim 10, wherein the mixture further comprises urea or melamine.

12. The method of claim 10, wherein the cross-linking agent is selected from the group consisting of formaldehyde, glutaraldehyde, di-acid chloride, and derivatives thereof.

13. The method of claim 10, wherein the copolymer is selected from the group consisting of ethylene maleic anhydride, whey protein isolate, sodium caseinate, a surfactant, and derivatives thereof.

14. The method of claim 1, wherein one or more of $R^1$, $R^2$, or $R^3$ is selected from the group consisting of

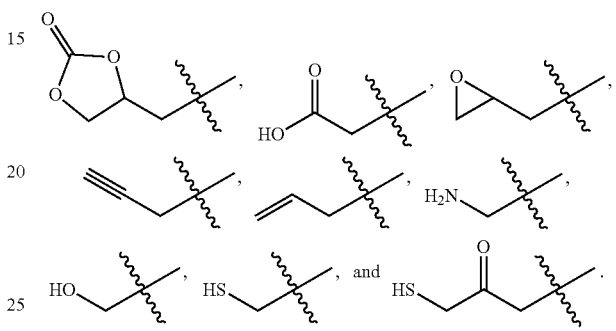

15. The method of claim 10, wherein the mixture further comprises $NH_4Cl$.

16. The method of claim 10, wherein at least a portion of the hexahydrotriazine-based compound is a reaction product of a formaldehyde and an amine.

17. The method of claim 1, wherein one or more of $R^1$, $R^2$, or $R^3$ is selected from the group consisting of

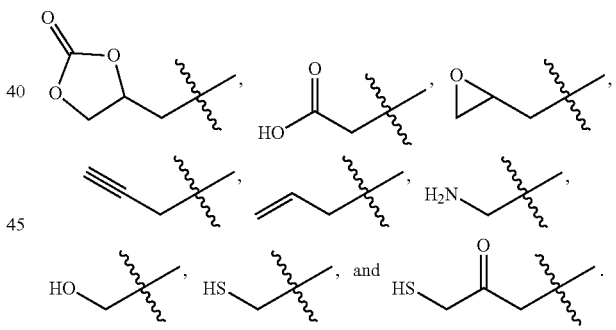

18. A method of making a microcapsule, comprising:
forming a mixture comprising a hexahydrotriazine-based compound, a cross-linking agent, a copolymer, and a solvent, the hexahydrotriazine-based compound comprising a hexahydrotriazine having the structure

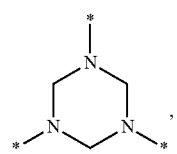

wherein at least one starred bond of the hexahydrotriazine represents a connection to a moiety of the hexahydrotriazine-based compound, the moiety having the structure

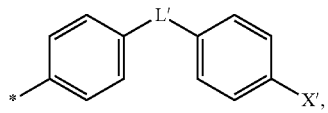

wherein:
- X' is selected from the group consisting of —OH, —O—, —NH$_2$, —NH—, —N(R$^1$)H, —N(R$^1$)—, —SH, —S—, —SO$_2$, —OR$^2$, and —R$^3$, and combinations thereof,
- L' is selected from the group consisting of —O—, —S—, —N(R$^4$)—, —N(H)—, —R$^5$—, and combinations thereof,
- one or more of R$^1$, R$^2$, or R$^3$ is selected from the group consisting of

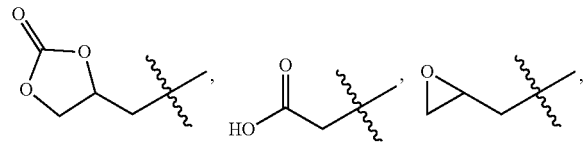

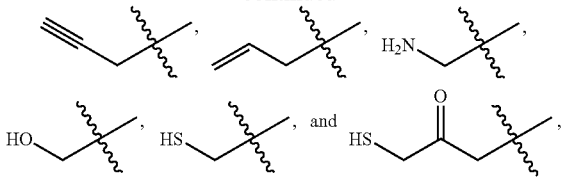

and

R$^4$ and R$^5$ independently comprises at least 1 carbon,
adjusting a pH of the mixture; and
adding a payload agent.

19. The method of claim 18, wherein the group is

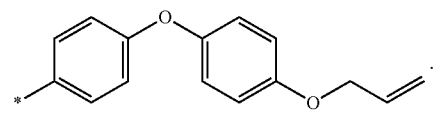 [SMILES: *c1ccc(Oc2ccc(OCC=C)cc2)cc1]

20. The method of claim 18, wherein at least a portion of the hexahydrotriazine-based compound is a reaction product of a formaldehyde and an amine.

* * * * *